United States Patent
Sava et al.

(10) Patent No.: US 6,762,161 B2
(45) Date of Patent: Jul. 13, 2004

(54) PROCESS AND COMPOSITION FOR CLEANING MEDICAL INSTRUMENTS COMPRISING PROTEASE AND QUATERNARY AMMONIUM DISINFECTANT

(75) Inventors: Alex Sava, Paddington (AU); Steven Kritzler, Cronulla (AU)

(73) Assignee: Novapharm Research (Australia) Pty LTD (AU)

( * ) Notice: Subject to any disclaimer, the term of this patent is extended or adjusted under 35 U.S.C. 154(b) by 0 days.

(21) Appl. No.: 10/257,088

(22) PCT Filed: Apr. 5, 2001

(86) PCT No.: PCT/AU01/00381

§ 371 (c)(1),
(2), (4) Date: Apr. 10, 2003

(87) PCT Pub. No.: WO01/76647

PCT Pub. Date: Oct. 18, 2001

(65) Prior Publication Data

US 2004/0029752 A1 Feb. 12, 2004

(30) Foreign Application Priority Data

Apr. 7, 2000 (AU) ............................................. PQ6791

(51) Int. Cl.[7] ............................. C11D 3/48; C11D 3/386
(52) U.S. Cl. ...................... 510/161; 510/382; 510/384; 510/391; 510/392; 510/504
(58) Field of Search .................................. 510/161, 382, 510/384, 391, 392, 504

(56) References Cited

U.S. PATENT DOCUMENTS

| | | |
|---|---|---|
| 4,867,797 A | 9/1989 | Thomasen et al. |
| 4,941,989 A | 7/1990 | Kramer et al. |
| 5,234,832 A | 8/1993 | Disch et al. |
| 5,356,555 A | 10/1994 | Huth et al. |
| 5,451,398 A | 9/1995 | Vigh |
| 5,489,531 A | 2/1996 | Benson |
| 5,576,278 A | 11/1996 | Van Duzee et al. |
| 5,723,421 A | 3/1998 | Chowhan et al. |
| 5,998,342 A | 12/1999 | Scoville, Jr. et al. |
| 6,010,996 A | 1/2000 | Hu et al. |

FOREIGN PATENT DOCUMENTS

| | | |
|---|---|---|
| EP | 0 384 666 B1 | 11/1994 |
| EP | 0 425 016 B1 | 12/1995 |
| JP | 4231054 | 8/1992 |
| JP | 9173426 | 7/1997 |
| WO | WO 00/12663 | 3/2000 |

*Primary Examiner*—Charles Boyer
(74) *Attorney, Agent, or Firm*—Jenkens & Gilchrist

(57) ABSTRACT

The invention relates to a method for cleaning a contaminated medical instrument including the step of immersing the instrument in a solution containing an enzyme based cleaning composition including a "hospital grade disinfectant". Compositions useful for cleaning contaminated medical instruments in accordance with the method include an enzyme, a quat biocide and an "activity protector", which may be for example, enzyme stabilizers, enzyme stabilizing systems, micelle formation modifiers and inhibitors, and combinations thereof.

29 Claims, No Drawings

PROCESS AND COMPOSITION FOR CLEANING MEDICAL INSTRUMENTS COMPRISING PROTEASE AND QUATERNARY AMMONIUM DISINFECTANT

CROSS REFERENCE TO RELATED APPLICATIONS

This application is a 371 of PCT/AU01/00381, filed Apr. 5, 2001, which claims priority to Australian Patent Application No. PQ6791, filed Apr. 7, 2000, both of which are incorporated by reference herein in their entirety.

FEDERALLY SPONSORED RESEARCH STATEMENT

Not applicable.

REFERENCE TO MICROFICHE APPENDIX

Not applicable.

FIELD OF THE INVENTION

This invention relates to a method of and composition for cleaning medical instruments. The method is suitable for use with endoscopes and is herein described with particular reference to that use, but it will be understood that the method is equally suitable for use with other instruments such as colonoscopes, laparascopes, other surgical, medical, biopsy, dental and such like instruments, parts of such instruments and similar paraphernalia (hereinafter collectively referred to as "medical instruments"). The invention is also applicable for treatment of instruments which are required merely to be disinfected for example hair-dressing tools, certain beauty parlour equipment, and the like.

BACKGROUND OF THE INVENTION

Endoscopes are increasingly being used in medical diagnosis and therapy When used as directed the endoscope becomes grossly soiled and massively infected with microorganisms which are present in body cavities, on the mucous membrane, and in the blood. Accordingly the instruments must be thoroughly cleaned and disinfected after each use. Endoscopes are precision instruments which are made from a combination of materials. They are difficult to clean in view of the sensitivity of the materials involved to chemical attack and because they have narrow lumens making access to and cleaning of interior surfaces difficult.

Until the last decade, it was common for soiled instruments to be placed on a towel or in a covered pan until they were sent to a centralised service where they were scrubbed, washed and either sterilised in a steam autoclave (if not heat sensitive) or chemically (e.g. with formaldehyde). In the last decade, there has arisen a particular concern to avoid transmission of very serious and sometimes fatal diseases such as may be carried in blood and tissue, for example hepatitis B, HIV, and other infections.

Nowadays, contaminated endoscopes and other medical instruments are typically treated in a first bath ("presoak" or "cleaning" bath) containing one or a combination of anionic and non ionic surfactants. The first bath may optionally include one, or a combination of enzymes, adapted to digest biological contaminants including cellular material, blood and other body fluids. Enzyme containing pre-soaking liquids are significantly more efficient in removing water insoluble and protein soils and are now considered the industry standard. In the case of surgical instruments requiring to be sterilised, the instruments are typically then removed from the first bath, washed free of enzyme solution and other residues, and then deposited in a second bath containing a chemical sterilizing agent (for example, glutaraldehyde). The first bath container is subsequently washed and then furnished with a fresh enzyme solution so that the process may be repeated. The necessity for separate cleaning and sterilizing baths arises since enzymes are denatured by all known sterilizing agents and since sterilizing agents are deactivated by enzymes (as enzymes are proteins). Accordingly it has to date proved impossible to provide a "single bath" cleaning and sterilizing treatment, although a two part system involving an enzyme treatment followed by addition of a phenolic disinfectant in the same bath has been proposed.

Sterilisation protocols are followed to prevent cross infection and therefore instruments used with one patient are not combined with those which may have been used with another in the presoak bath. It is noteworthy that the presoak is not passive. Staff are instructed to syringe detergent liquor through all the lumens, to brush biopsy channels, etc. A colonoscope requires up to 14 manual brushing-syringing-plugging-unplugging operations. It is usual for staff to wear latex gloves when handling instruments into or out of the baths and when performing such like operations.

The present inventor has observed that currently used procedures, while effective for preventing crossinfection between patients, in fact exposes medical and/or hospital staff to hitherto unrecognised health and safety risks. By virtue that the enzymes of the first bath digest the biological secretions holding the microorganisms, thus releasing them within the bath, and surfactants efficiently disperse them, the fluid content of the first bath is itself readily contaminated to high levels with infectious material. Contrary to the belief of some hospital staff, enzymes do not kill bacteria but rather release them. The present inventor has measured bacterial counts in excess of $1 \times 10^9$ colony forming units ("cfu") per sq. cm. on instruments entering the first bath.

Staff are therefore at risk of infection (i) from splashes from the first bath either during scrubbing to release contaminants or during draining the first bath (or from splashes if an instrument is accidentally dropped into the bath), (ii) from glove failures (latex gloves have a "pinhole" failure rate of about 12%), (iii) from accidental glove immersion above the wrist line, (iv) from finger stick incidents in the bath resulting in glove and sometimes dermal penetration, (v) from aerosols created by brushes and syringes. In addition the wall surface of the first bath remains contaminated after the bath has been emptied and if not itself disinfected may be handled by unprotected staff. The last mentioned risk may be minimised by performing the sterilisation step immediately after the digestion step in the same container, but this does not avoid any of the other hitherto unrecognised risks and is wasteful in use of excess sterilant.

In some cases instruments may not be required to be sterilised, for example with spatulas, and holders which do not penetrate the body tissue, hair dressing implements and the like, it may be sufficient to disinfect the instruments to an appropriate standard. In such cases it would be desirable to provide a cleaning and disinfecting treatment capable of meeting the required standards with a single composition.

Any discussion of the prior art herein is not to be construed as indicative of the state of the common general knowledge in the field.

It is the object of the invention to avoid or ameliorate the above discussed disadvantages of prior art, or at least provide a commercial alternative to the prior art.

It is an object of preferred embodiments of the present invention to avoid or at least ameliorate the risk of infection to persons cleaning medical instruments by such procedures.

It is a further object of at least some of the preferred embodiments to provide a single step cleaning and disinfecting composition for use in cleaning medical instruments.

Preferred embodiments of the invention also address the risk of cross infection of instruments by virtue of multiplication of microorganisms, if any, which remain on the bath walls after each cycle of instrument cleaning.

It is an object of some embodiments of the invention to provide simple means for cleaning and disinfecting surfaces which require to be disinfected.

BRIEF DESCRIPTION OF THE DRAWINGS

Not applicable.

DETAILED DESCRIPTION OF THE INVENTION

According to a first aspect the invention provides a method for reducing the risk to health care workers when cleaning a medical instrument contaminated with an organic load including protein, said method comprising the step of treating the contaminated instrument with a liquid composition including a protease, a monoquaternary ammonium disinfectant and an activity protector, the activity protector being of a kind and in a concentration selected so that the liquid provides hospital grade disinfection (as herein defined) in the presence of said protease and said load.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

In preferred embodiments of the invention the treating step includes immersion of the instrument in the solution and is followed by a second treatment in which the instrument is sterilised. However for some disinfecting purposes it may be sufficient to rinse the instrument with sterile water after the first treatment or to provide a further disinfecting treatment.

In Australia, disinfectants are graded according to tests specified by the TGA in order of decreasing efficacy as Grade B "Hospital Dirty", Grade A "Hospital Clean", Grade C "household/commercial". A copy of "The TGA Disinfectant Test" is annexed. The TGA tests are specified as TGO 54. Similar tests and classifications are applicable in other countries. The term "hospital grade" disinfectant is herein used to refer to disinfectants passing the Grade A test, i.e. a "hospital grade" disinfectant must be at least Hospital Grade A. The TGA specification requires that a "hospital grade disinfectant is able to give at least an 8 or 9 log reduction in inoculum density within 8 minutes.

The applicant has discovered a method whereby a hospital grade disinfectant, preferably a quaternary ammonium biocide ("quat. biocide") can be included in a cleaning composition which in use comes in contact with proteinacious material such as blood and other biological contaminants such as are encountered in cleaning endoscopes and other surgical instruments.

Hitherto it has been accepted that quat. biocides are instantaneously deactivated by protein and certain ions such as those found in hard water. It is therefore surprising that a grade A disinfectant can be effective in such an environment as is made possible by the present invention. Even more surprisingly, in preferred embodiments of the invention the quat. biocide is in the form of a liquid concentrate which retains its biocidal activity in prolonged shelf-storage in contact with one or more enzymes which are also proteins which normally would be expected to quickly deactivate the quat. biocide. Surprisingly, also, the enzymes are not irreversibly denatured. The liquid concentrate is readily diluted with water for use.

It will be appreciated that a first treatment according to the invention does not result in disinfection or sterilisation of the instruments and for that purpose a subsequent disinfection or sterilizing treatment may be required. However the presence of an effective disinfectant in the enzyme bath is sufficient to prevent multiplication of microorganisms in the bath and to afford a degree of protection for staff not previously available from accidental infection in the risk circumstances previously outlined.

According to a second aspect the present invention provides a liquid composition for use in cleaning a medical instrument contaminated with an organic load including a protein, said composition including:

a protease a mono quaternary biocide; and an activity protector of a kind and in a concentration selected so that the liquid provides hospital grade disinfection (as herein defined) in the presence of said protease and said load.

The "activity protector" is described more particularly hereinafter

In highly preferred embodiments, compositions according to the second aspect also include a non-ionic surfactant;

Desirably the "activity protector" or "activity protector" system is present in a concentration sufficient that the quaternary ammonium biocide is effective in use to provide "hospital grade A" disinfection (as herein defined) of the bath in the presence of the at least one enzyme and of a typical proteinaceous load in the bath.

The "activity protector" is a composition selected from (1) compositions known to be effective in stabilizing enzymes in liquid aqueous solutions, including enzyme stabilizing compounds and systems, (2) selected "micelle inhibitors", and mixtures of (1) and (2). In preferred embodiments of the invention the "activity protector" is an enzyme stabilizer and more particularly is a suitable concentration of boron anions. Desirably these are solvated in a polyol and may be combined with enzyme stabilizing synergists or adjuvants forming an enzyme stabilizing system. Preferred "micelle inhibitors" include species known to modify as well as to inhibit micelle formation and may be selected from water miscible solvents such as C1–C6 alkanols, C1–C6 diols, C2–C24 alkylene glycol ethers, alkylene glycol alkyl ethers, and mixtures thereof. A highly preferred micelle inhibitor is di-(propylene glycol) methyl ether. ("DPM") and analogues thereof which modify micelle formation. It is especially preferred to combine the use of borate ions with DPM which has been found by the present inventor synergistically to enhance the biocidal activity protection conferred on the quat. biocide without irreversibly denaturing the enzyme.

It is highly preferred that the quat biocide is an aryl quat compound, preferably benzalkonium halide.

It is well known that enzymes may become denatured in storage, in the presence of other enzymes, and/or in the presence of antagonistic anions such as for example anionic surfactants, quaternary ammonium compounds and detergency "builders". A number of enzyme stabilizing systems have been developed and are well known in the enzyme formulation art. An example of an "enzyme stabilizing system" is a boron compound (e.g. boric acid) which in the past has been used alone or with selected other adjuvants and or synergists (e.g. polyfunctional amino compounds, antioxidants, etc) to protect proteolytic and other enzymes in storage and in various products. It has been theorised that an enzyme stabilizing system such as boron and calcium form intramolecular bonds which effectively cross-link or staple an enzyme molecule so as to hold it in its active spatial configuration. Enzyme stabilizers have not hitherto been used to protect the biocidal activity of a quat. biocide. The present invention is based on the surprising discovery that at least some enzyme stabilizing systems are effective in protecting the biocidal activity of quat. biocides in the presence of protein.

In accord with the present invention the ratio of "activity protector" e.g. boron to quat. biocide is preferably chosen to substantially to minimise the Minimum Inhibitory Concentration ("MIC") of quat. biocide in the presence of the enzymes in the formulation and at a given level of protein load. MIC is a measure of the minimum concentration of the biocide which succeeds in preventing bacterial growth in a culture during a specified time period, for example 24 hrs. Details of the MIC test are shown in "Bailey & Scott 'Diagnostic Microbiology', $8^{th}$ edition, 1990 at page 177. The TGA tests are specified at TGO 54 annexed. MIC tests referred to herein are conducted over 24 hrs.

In the present case in which an enzyme is present in addition to the quat. biocide and in which it is desired to retain the enzymatic activity of the enzyme as well as the biocidal activity of the quat, biocide then the quantity of "activity protector" required will need to be greater than that required merely to protect the enzyme and will need to be sufficient both to stabilise the enzyme and protect the biocidal activity of the quat. biocide. Moreover as the composition is anticipated to come into contact with an external proteinaceous load (from contaminants in the surgical instruments bath) then the "activity protector" concentration will need to be greater still.

The inventor has discovered that boron surprisingly protects a quaternary biocide from deactivation by a protein in such a way and to such an extent that the MIC of the biocide is not increased in the presence of a protein. In preferred embodiments of the invention the MIC is dramatically reduced, for example, more than halved notwithstanding the presence of up to 2 wt. % based on the weight of solution, of protein. This allows the formulation of a wide range of new and useful compositions which remain effective as disinfectants or antibacterials in circumstances in which the prior art would be significantly less effective or not effective at all.

The invention also enables storage-stable liquid biocidally effective compositions to be prepared with a lower concentration of quat. biocide and at much lower cost. By "shelf stable" is meant that the composition retains at least 50% of its biocidal efficacy after 12 months storage in a sealed container at 18–25° C. Preferred embodiments of the invention retain better than 98% biocidal efficacy under these conditions.

Without wishing to be bound by theory, the inventor speculates that polymeric borate ions associate with the cationic quat. biocide, thus protecting the quat biocide from combining with proteins. When the formulation is diluted the polymeric ions become unstable and release the quat biocide for disinfection. Alternatively, it may be that the biocidal activity of the quat. biocide significantly relates to denaturing proteins of cell membranes and that boron complexes with charged groups of non-living proteins and prevents wasting quat. on denaturing non-living proteins. However as enzymes are structurally quite different from quat. biocides, and as the complete mechanism by which quat. biocides kill bacteria is also uncertain, it was not previously predictable that any enzyme stabilizer would be effective in maintaining the biocidal activity of a quat. biocide (an enzyme antagonist). The mechanism by which the activity of the quat biocide is maintained may be different from that whereby the enzyme is stabilised.

Other "activity protectors" are discussed hereinafter.

According to a third aspect the invention provides a composition according to the second aspect further including a nonionic surfactant.

Preferably the nonionic surfactant is one or a combination of surfactants selected from the group consisting of ethoxylates or propoxylates and block copolymer of these.

A highly preferred embodiment of the invention, provides an economical effective cleaning and disinfecting composition which contains enzymes, is shelf stable in storage in concentrated form, is readily diluted to a working concentration and remains biocidal in use in the presence of protein. Desirably the working dilution is effective in use as a Hospital Grade A disinfectant.

The invention will now be more particularly described by way of example only with reference to various embodiments.

Example 1 is a composition which is a concentrate stable in storage but which in use is diluted with water from 200:1 to 1000:1 (i.e. 200 or 1000 parts/wt water to 1 part/wt concentrate) The composition is useful for comparing the effects of addition of various components to a Quat. biocide

EXAMPLE 1

|  | g/l |
|---|---|
| Benzyl dimethyl ammonium chloride, CAS 68424-85-1 | 150 |
| Sodium teraborate decahydrate, CAS 12007-42-0 | 30 |
| Glycerin, CAS 56-81-5 | 25 |
| Terric GN9 (note 1) | 200 |
| Dipropylene Glycol Methyl Ether CAS 34590-94-8 | 100 |
| Water balance to | 1000 |

Note 1:
Terric GN9 is ethoxylated nonylphenol available from ORICA and is a non-ionic surfactant.

Preparation

The sodium tetraborate is dissolved/suspended in the glycerol at 80° C. The quaternary biocide and Terric GN9 (non-ionic detergent) are combined with the DPM and the pH adjusted with e.g. acetic acid to pH 7.2–7.3. The borate/glycerin solution is then combined with the quaternary biocide.

EXAMPLE 2

Example 2 is identical to example 1 but includes 0.1% of subtilisin (0.1% protease enzyme).

Table 1 shows MIC results obtained with various combinations of components of example 1 and example 2 in the absence of the boron and, in accordance with the invention, in the presence off the boron. In Table 1 "Quat" is an abbreviation for benzyl dimethyl ammonium chloride.

TABLE 1

| composition | MIC, ppm (no boron) | MIC, ppm (with boron) |
|---|---|---|
| A | | |
| 1 quat (prior art) | 20 | 12 |
| 2 quat + DPM | 16 | 8 |
| 3 quat + GN9 | 25 | 8 |
| 4 quat + DPM + GN9 | 16 | <8 |
| B | | |
| 1 quat + subtilisin (0.1% protease enzyme) | 50 | 25 |
| 2 quat + DPM + enzyme | 25 | 12 |
| 3 quat + GN9 + enzyme | 25 | 12 |
| 4 quat + dpm + GN9 + enzyme | 25 | 8 |

Table 1 part A compares the MIC of various quaternary ammonium biocidal compositions in the absence of boron and in the presence of boron but in the absence of protein. MIC was measured by test method described in Bailey and Scott Diagnostic Microbiology, 8$^{th}$ edition, 1990, p.177 using one of the most resistant to QUATs strains of *Pseudomonas aeroginosa* ATCC No. 15442.

Table 1 exp. 3 shows that Terric GN9 deactivates the quat. biocide as would be expected. Unexpectedly, DPM enhances the activity of a quat. even in the presence of GN9, while in each case the combination with Boron produces a marked improvement in biocidal efficacy in comparison with the combination in the absence of boron.

Table 1 part B shows the results in the presence of proteolitic enzyme subtilisin. As is apparent from the table the presence of the enzyme in the absence of boron results in a considerable reduction in efficacy of the disinfectant.

It is noteworthy that there is an improvement in efficacy of the quaternary biocide (reduction in MIC) in the presence of DPM even in the presence of the deactivator Terric GN9. However the results are significantly better with boron than without. The combination of DPM with boron synergistically improves the biocidal activity protection of the boron in comparison with compositions lacking boron or DPM (even in the presence of Terric GN9) achieving an end result of higher efficacy in the presence of the enzyme and the Terric GN9 than obtainable with the quat. biocide in the presence of 0.1% of subtilisin in the absence of boron.

A preferred embodiment of the invention is shown in example 3. The composition of example 3 is a concentrate intended for dilution 1 part/wt concentrate in 200 parts/wt water. The composition is intended for application as a pre-soak for surgical instruments.

EXAMPLE 3

| Component | % w/w |
|---|---|
| A. | |
| Nonyl phenol ethoxylate (Terric GN9) | 3 |
| Di (propylene glycol) methyl ether | 5 |
| Perfume | .1 |
| Water | 15 |
| B. | |
| Sodium tetraborate decahydrate | 6 |
| Glycerol | 4 |
| water | 5 |
| C. | |
| Acetic acid to pH 7.2 – 7.3 | |
| D. | |
| Ethylene Glycol | 5 |
| (10% subtilisin) Alcalase 2.5 DL | 3 |
| E. | |
| Benzalkonium Chloride 80% | 30 |
| Water | to 100 |

Premix Borax with hot water and glycerin, add to A, adjust pH, let the mixture cool down 30° C. and then slowly add premixed ingredients D. Then add water premixed with Benzalkonium Chloride 80%.

The composition is stable for at least 1 year prior to use when stored in a sealed container at 18–25° C. and when diluted with water 200:1 is biocidally effective in use for at least 24 hrs. achieving "Hospital GRADE A" disinfection.

The composition is also biocidally effective at dilutions of less than 200:1, for example, 20:1.

EXAMPLE 4

Example 4. In-surgery comparison of detergent concentrates for pre-cleaning of flexible colonoscopes.

An in-vivo evaluation was performed in a surgery randomly over a period of nine months on 105 colonoscopes after colonoscopy procedures.

Colonoscopes were soaked in 10 L of diluted 200:1 concentrates of the following detergents:

1. 15% sodium laurel sulphate +20% Dodecyl benzene sulphonic acid at pH=9
2. 10% Dodecyl benzene sulphonic acid 10% Nonyl phenol ethoxylate (Terric GN9), 10% Alcalase 2.5 DL (subtilisin)
3. Composition described in example 3.

Total soaking time—10 minutes. This was followed by rinsing with 10 L of sterile distilled water.

The level of bacterial contamination of:
washing liquor—liquid in the bath (B)
biopsy channels (C)
surface of the endoscope (S)
were determined by plating of
the washing liquor (B),
10 mL of water syringed through the biopsy channel (C)
and cotton swabs after wiping 5 sq. sm of the endoscope surface (S)
of serially diluted samples onto Macconkey agar plates.

The bacterial contamination of the same parts of colonoscope and the washing liquor when instruments were soaked in sterile distilled water were used as control.

Table 2. Total bacteria counts of the contaminated surfaces on colonoscopes after soaking in detergents (statistically processed average of 105 samples, Statistical significance (t-test) was set at $p<0.05$):

TABLE 2

|   | B washing liquor | C Biopsy channel | S Surface |
|---|---|---|---|
| 1 | $2.2 \times 10^9$ | $6.2 \times 10^3$ | $9.5 \times 10^3$ |
| 2 | $4.0 \times 10^9$ | $5.1 \times 10^1$ | $2.9 \times 10^1$ |
| 3 | 0 | 0 | 0 |
| Control | $3.7 \times 10^8$ | $4.1 \times 10^6$ | $9.1 \times 10^4$ |

This clearly indicates that concentrates that contain no quat. biocide only release (disperse) the bacteria and soils, creating alarmingly high bacterial contamination in cleaning baths and leaving significant amount of viable bacteria on colonoscopes. Using the present invention, one achieves a safe working environment. In the case of an instrument that is intended for contact with unbroken skin, the concentrate may be used for a one-step cleaning disinfection procedure.

The Quat. Biocide

The invention has been exemplified by reference to alkyl benzyl dimethyl ammonium chloride (also known as benzalkonium chloride) as the highly preferred quat. biocide. However those skilled in the art will recognise that other monomeric quaternary ammonium antimicrobial compounds may be used.

It is preferred that the quaternary ammonium antimicrobial compound is selected from the group having a general formula:

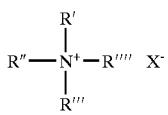

wherein R' R" R'" R"" are alkyl radicals that may be the same or different, substituted or unsubstituted, branched or unbranched, and cyclic or acyclic. X is any anion but preferably a halogen, more preferable chlorine or bromine.

Highly preferred antimicrobial compounds are mono-long chain, tri-short chain, tetralkyl ammonium compounds, di-long-chain, di-short chain tetralkyl ammonium compounds and mixtures thereof, where by "long" chain is meant about C6–C30 alkyl, and by "short" chain is meant C1–C5 alkyl, preferably C1–C3, or benzyl, or C1–C3 alkylbenzyl. Examples include monoalkyltrimethyl ammonium salts such as cetyltrimethyl ammonium bromide (CTAB), monoalkyldimethylbenzyl compounds or dialkylbenzyl compounds. Quat. biocides such as chlorhexadine gluconate may be employed.

The most highly preferred compounds for use in the invention have at least one benzyl radical which may be a substituted benzyl. Examples include C8–C22 dimethyl benzyl ammonium chloride, C8–C22 dimethyl ethyl benzyl ammonium chloride and di-C6–C20 alkyl dimethyl ammonium chloride The quaternary ammonium compound is incorporated for broad spectrum (gram positive and gram negative) antibacterial properties and should be present at least in an amount which would be effective for that purpose in the absence of protein or other deactivator. It is surprising that compositions according to the invention have excellent shelf stability both in concentrated and dilute form.

Activity Protector

According to the invention the biocidal activity of the quaternary biocide is in use protected by an "activity protector" which is a composition (an ion, compound, or combination thereof) selected from the group of known "enzyme stabilizing systems" including both reversible and irreversible enzyme inhibitors such as described in "Handbook of Enzyme Inhibitors", Zollner H., $2^{nd}$ ed. VCH 1993. The preferred activity protector is a boron compound or more preferably a mixture of a boron compound and a polyol. The boron compound may for example be boric acid, boric oxide, borax, or sodium ortho-, meta-, or pyro-borate. In some formulations it may be desirable to use a perborate, such as sodium perborate to obtain a bleaching effect. The most preferred boron source is sodium tetraborate. The protective effect of the boron compound may be enhanced by the presence of formate, or calcium ion, or by polyfunctional amino compounds such as di- or tri-ethanolamine. Other activity protection enhancers, or adjuvants, include anions such as phosphates, citrates, sulphates and sequestering agents such as used as water softeners such as EDTA.

In systems which use boron to stabilise enzymes the addition of antioxidants and/or polyfunctional amino compounds has been reported to produce a synergistic enzyme stabilizing effect and the use of such enzyme stabilizer synergists in the present system is contemplated. The term "enzyme stabilizer systems" is used herein to denote combinations of stabilizers with enhancers, adjuvants and/or synergists and the like Polyol The quat. biocide activity protector desirably includes a polyol.

The polyol is preferably one containing from 2–6 hydroxyl groups and containing only C, H, and O atoms. Typical examples are ethylene glycol, propylene glycol 1,2 propanediol, butyleneglycol and most preferably glycerol. Other polyols such as mannitol, sorbitol, erythritol, glucose, fructose, lactose, etc may also be useful. The polyol is selected to solvate the boron and increase its ionic strength in the composition and will usually be present in an amount at least equal to the amount of boron compound.

Micelle Inhibitors

A water miscible solvent is desirably included to assist in solubilising the components and/or substances with which the composition comes into contact depending on its intended use and avoid or inhibit or modify micelle formation. This acts synergistically as an "activity protector" as well as apparently in some instances enhancing biocidal activity in its own right.

Preferably a water miscible solvent is selected from C1–C6 alkanol, C1–C6 diols, C3–C24 alkylene glycol ethers, alkylene glycol alky ethers and mixtures thereof. A highly preferred solvent is di (propylene glycol) methyl ether. Other known micelle antagonists include borates, lactates, citrates, tartrates.

Enzymes

The boron stabilizer is added in an amount required to prevent deactivation of the enzyme in the presence of protein. Surprisingly it has been found possible to include one or more enzymes in compositions according to the invention and to provide sufficient boron in the composition both to protect the quat. biocide from deactivation by the enzyme, and to protect the quat. biocide from deactivation by an additional protein (i.e. additional to the enzyme) and also to stabilise the enzymes against being denatured by the quat. It may be that a complex of the quat (e.g. with the protein) participates in reversibly protecting the enzyme. The enzymes may for example be proteolytic enzymes or selected from carbohydrases, esterases, hydrazes, amylases, proteases, catalases, lipases, amylases, cellulases, peroxidases, invertases, and the like together with mixtures thereof. The use of proteases is preferred, and of subtisilin is highly preferred.

Surfactant

In preferred embodiments of the invention a surfactant is present. The surfactant is a non-ionic surfactant and it is highly preferred that it be selected from alkoxylated alcohols or alkoxylated phenol ethers or mixtures of them. Other semipolar nonionics such as trialkyl amine oxides may also be useful. Examples of alkoxylated phenol ethers include octyl or nonyl phenol ether with varying degrees of alkoxylation. 6–10 moles of ethylene oxide per mole of phenol is preferred. The alkyl group can vary from C6–C16 The more highly preferred are low alkoxylated nonionics having 6–25 moles of ethylene oxide and/or propylene oxide per molecule.

The alkoxylated alcohols include ethoxylated and propoxylated C6–C16 alcohols with about 2–10 moles of ethylene oxide, or 1–10 and 1–10 moles of ethylene and propylene oxide per mole of alcohol respectively.

If amine oxides are used these may be mono-long chain, di-short chain, trialkylamine oxides and can be ethoxylated or propoxylated, an example is lauryl amine oxide, or cocoamidopropyldimethylamine oxide.

The quantity of surfactant is chosen so as to provide sufficient detergency for soil removal, and will typically be in the range of from 0.05% to 10% of the concentrate more preferably about 0.5% to 6% and most preferably from 2%–4%

Treatment with the disinfectant cleaner herein described may be followed by sterilisation using heat, chemicals, or any other suitable sterilizing system.

However if sterilisation (complete kill of viable organisms) is not required, an adequate level of disinfection may be obtainable by rinsing with sterile water or other sterile solvent Hospital Grade B disinfection may be obtained merely by rinsing with sterile water after the treatment herein described.

The fact that certain monomeric quat. biocides do not require to be rinsed even from food-contacting surfaces when applied at low levels provides an opportunity to formulate single-step cleaners/disinfectants useful on certain implements for dental use, denture cleaners and the like.

The invention is herein described with particular reference to boron as the "activity protector" and quaternary ammonium biocides. It may be that not all enzyme stabilizer systems are effective as quat. biocide activity protectors, but those which are and are not effective can be determined by routine screening based upon the teaching hereof.

It will also be understood that while the invention has been described with reference to the use of quat. biocides in the cleaning bath to prevent microorganism multiplication and protect staff, the concept of including an effective biocide in the cleaning solution at a level which is at least biostatic could be practiced by use of other biocidal systems, and such systems are within the scope of the invention herein disclosed. The invention may be embodied in many forms which will be apparent to those skilled in the arts of formulation, based upon the teaching herein contained.

Schedule 1

The TGA Disinfectant Test

This test method has been reproduced with the kind permission of the author and publisher from an original paper published in the "Australian Journal of Hospital Pharmacy", Vol 8, No 4; 1978 (152–155).

1. Principle

The method, as applied to Hospital Grade Disinfectants or Sanitisers, is essentially that given by Kelsey & Maurer (1) for testing disinfectant performance. It is set out in a form suitable for attachment to a regulatory minimum standard for disinfectants and antiseptics. For wider application of the test refer to supplementary note A.

The disinfectant is tested at the dilution recommended by the manufacturer on the product label. The test consists of challenging the diluted disinfectant with bacterial inoculum, withdrawing a sample after a given time and culturing the sample in a suitable recovery medium. After this sampling, the mixture is again challenged by a second inoculum and after a second interval is again sampled for culturing. The sample is passed or failed according to the extent of growth shown in the two cultures sampled. The test may be performed with or without the addition of sterile yeast as an organic soil. (Options B and A respectively) or both, according to the use-situations advocated on the label of the product under test.

TABLE 3

Selection of test parameters for classes of disinfectant and antiseptic using the TGA Disinfectant Test.

| Class of product | Organisms used in the test | Test option for resuspension of centrifuged organisms | Number of challenges | Inoculum density |
|---|---|---|---|---|
| Disinfectant - hospital grade: Sanitiser | Ps. aeruginosa Pr. Vulgaris E. Coli S. aureus | A ("clean" conditions) B ("dirty" conditions) | 2 | $2 \times 10^8$–$2 \times 10^9$ |
| Disinfectant - household or commercial grade | E. coli S. aureus | C | 1 | $2 \times 10^8$–$2 \times 10^9$ |
| Antiseptic (excluding those for intact skin only) | Ps. aeruginosa Pr. Vulgaris E. coli S. aureus | D | 1 | $1 \times 10^6$–$1 \times 10^7$ |

For Household Grade disinfectants, the first two organisms listed and the second challenge are omitted, while Option C (nutrient broth) is selected as the choice of simulated soil. For antiseptics, the second challenge is again omitted, while Option D (serum) is selected as the choice of soil.

2. Media

All media must be contained in capped glass containers. Where media are stored, the containers must be sealed tightly or refrigerated.

2.1 Sterile Hard Water 2.1.1 Dissolve 0.304 g anhydrous calcium chloride and 0.065 g anhydrous magnesium chloride in glass-distilled water, and make up to one liter.

2.1.2 Dispense into glass containers and sterilize by autoclaving at 121°±1° C. for 15 minutes.

2.2 Yeast Suspension 2.2.1 Weight 200 g of moist compressed baker's yeast. Cream by the gradual addition of sterile hard water using a heavy glass rod for stirring. Decant the creamed portion into a flask, add more water to any lumpy residue remaining and repeat the creaming and decantation until no residue remains and 500 ml of water has been used.

2.2.2 Shake the contents of the flask vigorously and strain through a 100-mesh sieve, breaking down any remaining lumps.

2.2.3. Add 500 ml sterile hard water, shake vigorously and adjust the pH to 6.9–7.1 with 1N Sodium hydroxide.

2.2.4 Transfer 50 ml, 100 ml or 200 ml of the yeast solution into screw-capped bottles.

2.2.5 Autoclave at 121°±1° C. for 15 minutes and allow the autoclave to cool without releasing pressure. Store cold but not freezing.

2.2.6 Dry two Petri dishes to constant weight. Into each, pipette 25 ml of sterilised yeast suspension, and dry to constant weight at 100° C. Calculate the average solids content of the suspension.

2.2.7 Before use, pipette 25 ml of the sterilised yeast suspension into a beaker. Determine the pH using the glass electrode, and determine the volume of 1N sodium hydroxide solution needed to adjust the pH to within the range 6.9 to 7.1.

2.2.8 Immediately before use, add to each bottle of sterilised yeast, a volume of sterile hard water and a volume of 1N sodium hydroxide calculated to adjust the concentration of dry yeast to 5.0% and the pH to within the range 6.9–7.1. Discard prepared yeast 3 months after preparation.

2.3 Medium for Growth of Test Organisms 2.3.1 Prepare a 10% w/v dextrose solution in distilled water, and sterilise by autoclaving at 121°±1° C. for 15 minutes. Cool to room temperature.

2.3.2 Prepare Wright and Mundy medium following the author's procedure (2) or from a commercial product of the same composition (Note B) and sterilise by autoclaving at 121°±1° C. for 15 minutes. Cool to room temperature.

2.3.3 To each litre of Wright and Mundy medium prepared in 2.3.2 add 10 ml sterile dextrose solution prepared in 2.3.1.

2.3.4 Aseptically dispense in either 10 ml or 15 ml amounts, as preferred.

2.3.5 This medium is referred to as Wright and Mundy dextrose medium.

2.4 Recovery Medium 2.4.1 Prepare nutrient broth as follows or from a commercial product of the same composition (Note B):

Add the following to 970 ml of water and dissolve by heating.

| | |
|---|---|
| Beef Extract Powder | 10 g |
| Peptone | 10 g |
| Sodium Chloride | 5 g |
| Adjust the pH to 8.0–8.4 using 1N Sodium Hydroxide. | |
| Boil for 10 minutes and filter. Cool. | |

2.4.2 To each litre of nutrient broth solution prepared in 2.4.1 add 30 g polysorbate 80 (Note B).

2.4.3 Adjust pH to 7.2–7.4, using 1N Sodium hydroxide.

2.4.4 Autoclave at 121°±1° C. for 15 minutes, and immediately shake well to disperse the polysorbate 80.

2.4.5 Dispense aseptically in 10 ml amounts into sterile capped glass tubes.

3. Test Inoculation 3.1 Test Organisms

The following 4 organisms are to be used, except where prescribed.

| | |
|---|---|
| *Pseudomonas aeruginosa* | NCTC 6749 |
| *Proteus vulgaris* | NCTC 4635 |
| *Escherichia coli* | NCTC 8196 |
| *Staphylococcus aureus* | NCTC 4163 |

3.2 Preparation of Inoculation 3.2.1 Incubate the contents of an ampoule of freeze-dried culture overnight at 37°±1° in Wright and Mundy dextrose medium.

3.2.2 Inoculate the incubated culture onto nutrient agar slopes in McCartney bottles. Store for up to 3 months at 4°±1° C.

3.2.3 At a suitable period before the test is to be conducted, sub-culture from an agar slope into 10 ml or 15 ml quantities of Wright and Mundy dextrose medium. Incubate at 37°±1° C. for 24±2 hours.

3.2.4 Sub-culture from the medium in 3.2.3 into fresh medium, using an inoculating loop of 4 mm in diameter. Incubate at 37°±1° C. for 24±2 hours.

3.2.5 Repeat step 3.2.4 daily. For the test procedure use only those cultures which have been sub-cultured at least 5, and not more than 14 times.

3.2.6 Filter test cultures of *P. aeruginosa* and *S. aureus* through sterile Whatmans No. 4 filter paper.

3.2.7 Centrifuge all test cultures until cells are compact, and remove supernatant with a Pasteur pipette.

3.2.8 Resuspend test organisms in the original volume of liquid (i.e. 10 ml or 15 ml), and shake for 1 minute with a few sterile glass beads.

3.2.8.1 For Option A, resuspend in sterile hard water.

3.2.8.2 For Option B, resuspend in a mixture of 4 parts yeast suspension (prepared as in 2.2) to 6 parts sterile hard water.

3.2.8.3 For Option C, resuspend in nutrient broth (prepared as in 2.4.1 and 2.4.3 and sterilised by autoclaving).

3.2.8.4. For Option D, resuspend in sterile hard water; dilute twice 1+9 in sterile hard water; then add 8 ml of the last dilution to 2 ml sheep serum previously inactivated at 56° C. for 20 mins and sterilised by filtration.

3.3 Enumeration of Inoculation

Immediately before testing, sample the resuspended inoculum and enumerate using 10-fold dilutions in quarter-strength Ringer's solution and the pour-plate technique. The number subsequently counted must represent not less than $2 \times 10^8$ or more than $2 \times 10^9$ organisms per millilitre (or $1 \times 10^8 - 1 \times 10^7$ using Option D) or the test is considered invalid. Retain tube containing $10^{-7}$ dilution for use in controls (7.3 and 7.4).

4. Disinfectant Dilutions

Quantitatively dilute a sample of the disinfectant to the specified extent, using sterile hard water as diluent. Use not less than 10 ml or 10 g of sample for the first dilution, and not less than 1 ml of any dilution to prepare subsequent dilutions. Make all dilutions in glass containers on the day of testing. The glass containers must be twice rinsed in glass-distilled water, and sterilised.

5. Temperature

Where air-conditioning does not maintain test solutions at $21° \pm 1°$ C., hold the containers in which the test is to be carried out in a waterbath at this temperature.

6. Test Procedure

Perform the following test using each of the four test organisms (3.1) except where the Standard directs otherwise. It is not necessary to test with all organisms simultaneously.

6.1 Add 3 ml of diluted disinfectant to a capped glass container.

6.2 Start a timing device. Immediately inoculate disinfectant with 1 ml of culture (prepared in 3.2) and mix by swirling.

6.3 At 8 minutes, subculture one drop (0.02 ml±0.002 ml) into each of 5 tubes containing recovery broth. To ensure delivery of 0.02 ml into the first tube of recovery broth at exactly 8 minutes, it will be necessary to withdraw a suitable amount from the disinfectant test mix shortly beforehand. This must be immediately preceded by vortexing. Surplus sample must be returned to the test mix (See Note D).

6.4 Except where prescribed, at 10 minutes, inoculating disinfectant with a further 1 ml of culture, and mix by vortexing.

6.5 Except where prescribed, at 18 minutes, proceed as in 6.3.

6.6 Mix the contents of all tubes of recovery broth by vortexing. Incubate at $37° \pm 1°$ C. for $48 \pm 2$ hours.

6.7 Examine for growth and record results.

6.8 For each test organism repeat steps 6.1–6.7 on each of 2 subsequent days, using fresh disinfectant dilution and a freshly prepared bacterial suspension.

7. Controls 7.1 Recovery broth contamination

Incubate one uninoculated tube of recovery broth at $37° \pm 1°$ C. for $48 \pm 2$ hours and examine for growth. If growth occurs, the test is considered invalid due to contamination of the recovery broth.

7.2 Disinfectant Contamination

To 1 tube of recovery broth, add 0.02 ml of diluted disinfectant. Incubate at $37° \pm 1°$ C. for $48 \pm 2$ hours. If growth occurs, the test is considered invalid. Growth in 7.2 but not 7.1 indicates contamination of the disinfectant test solution.

7.3 Fertility Test

To 1 tube of recovery broth, add 1.0 ml of the $10^{-7}$ dilution retained in 3.3. Incubate at $37° \pm 1°$ C. for $48 \pm 2$ hours and examine for growth. If no growth occurs, the test is considered invalid.

7.4 Inactivator Efficacy

To 1 tube of recovery broth, add 0.02 ml of diluted disinfectant and 1.0 ml of the $10^{-7}$ dilution retained in 3.3. Incubate at $37° \pm 1°$ C. for $48 \pm 2$ hours, and examine for growth. If no growth occurs, the test is considered invalid. Growth in 7.3 but not in 7.4 indicates inadequate inactivation of the disinfectant.

8. Procedure in Case of Invalid Controls

When any control renders the test invalid, the test is to be repeated. Fresh recovery broth is to be used if growth occurred in control 7.1 or if no growth occurred in controls 7.3 or 7.4.

Should disinfectant contamination be indicated by control 7.2 on both occasions, the disinfectant is considered to fail the test. Should inadequate inactivation of the disinfectant be indicated by control 7.4 on both occasions, the test is considered invalid (Note C).

9. Results

The dilution test passes the test if there is no apparent growth in at least two out of the five recovery broths specified in 6.3 and no apparent growth in at least two of the five recovery broths specified in 6.5 on all three occasions, using all four organisms.

10. REFERENCES (1) Kelsey, J. C. and Maurer Isobel, M. Pharmaceutical Journal (UK) 213: 528–530, (1974).

(2) Wright Eleanore, S. and Mundy, R. A. Journal of Bacteriology 80: 279–280, (1960).

11. Supplementary Notes

A. For investigational, developmental or comparative purposes, it will be useful to add a third challenge thus performing a true capacity test, and to test at dilutions above and below the prescribed dilution. In such cases, Kelsey & Maurer's recommendations regarding the timing and organisation of the test should be carefully consulted. Abbreviations of the test may be considered for the routine test of production batches.

B. Wright & Mundy medium is commercially available as "Bacto Synthetic Broth", A.O.A.C. Code No. 0352 (Difco Ltd.). The nutrient broth to be used is available as "Nutrient Broth—No. 2" (Oxoid Ltd.).

C. Where inadequate inactivation is indicated, investigations should be conducted to find an effective inactivator. Refer Mackinnon, I. H. J. Hyg (London) 73: 189–195, (1974).

D. The Oxford P-7000 sampler system with disposable plastic tips is recommended for the withdrawal of samples for subculturing.

Schedule 2

| Schedule 2 Acceptable Common Names | |
|---|---|
| Descriptive Name | Common Names |
| Sterilant | Sterilant |
| Instrument Grade - high level disinfectant | Instrument grade - High level disinfectant or High Level Instrument Disinfectant or Instrument Disinfectant - high level or High Level Instrument Grade Disinfectant or High Level Disinfectant or Instrument Grade Disinfectant |
| Instrument Grade - intermediate level disinfectant | Instrument Grade - intermediate level disinfectant or Intermediate Level disinfectant or Instrument grade Disinfectant, or Intermediate Level Instrument Disinfectant or Intermediate Level Disinfectant |

-continued

Schedule 2
Acceptable Common Names

| Descriptive Name | Common Names |
| --- | --- |
| Instrument Grade - low level disinfectant | Instrument Grade - low level disinfectant or Low Level Instrument Grade Disinfectant, or Low Level Disinfectant, or Instrument Grade Disinfectant - low level |
| Hospital grade disinfectant (see Surface spray below if primarily for use as a spray) | Disinfectant - hospital grade Hospital Grade Disinfectant |
| Household/Commercial grade disinfectant (see Surface spray below if primarily for use as a spray) | Disinfectant - household grade, or Disinfectant - commercial grade, or Household Grade Disinfectant, or Commercial Grade Disinfectant |
| Surface spray disinfectant | Surface spray disinfectant - hospital grade, or Surface spray disinfectant - household grade, or Surface spray disinfectant - commercial grade |
| Antibacterial clothes preparation | Antibacterial (together with a word or words indicating the nature of the product) |
| Sanitary fluid | Sanitary fluid |
| Sanitary powder | Sanitary powder |
| Sanitiser | Sanitiser, or Sanitising Solution, or Antibacterial (together with a word or words indicating the nature of the product) |

What is claimed is:

1. A method for reducing the risk to health care workers when cleaning a medical instrument contaminated with an organic load including protein, said method comprising the step of treating the contaminated instrument with a liquid composition comprising a protease, a monoquaternary ammonium disinfectant and an activity protector, the activity protector being of a kind and in a concentration selected so that the liquid provides hospital grade disinfection (as herein defined) in the presence of said protease and said load.

2. A method according to claim 1 further comprising the step of sterilizing the instrument.

3. A method according to claim 1 further comprising the step of rinsing the instrument.

4. A method according to claim 1 wherein the composition further comprises one or more enzymes selected from the group consisting of proteolytic enzymes, carbohydrases, esterases, hydrazes, amylases, catalases, lipases, amylases, cellulases, peroxidases, invertases and mixtures thereof.

5. A method according to claim 1 wherein the activity protector is or comprises a micelle formation inhibitor.

6. A method according to claim 1 wherein the monoquaternary biocide is a monomeric quaternary ammonium antimicrobial compound selected from the group having a general formula:

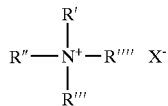

wherein R', R", R''', R'''' are alkyl radicals that may be the same or different, substituted or unsubstituted, branched or unbranched, and cyclic or acyclic, and X is any anion.

7. A method according to claim 6 wherein X is chlorine, bromine or other halogen.

8. A method according to claim 6 wherein the quaternary biocide is selected from the group consisting of mono-long-alkyl chain, tri-short chain, tetralkyl ammonium compounds; di-long-chain, di-short chain tetralkyl ammonium compounds and mixtures thereof.

9. A method according to claim 8 wherein the quaternary biocide is selected from the group consisting of monoalkyltrimethyl ammonium salts, monoalkyldimethylbenzyl compounds, dialkylbenzyl compounds and Quaternary gluconates.

10. A method according to claim 9 wherein the biocide is selected from the group consisting of C8 to C22 dimethyl benzyl ammonium chloride, C8–C22 dimethyl ethyl benzyl ammonium chloride and di-C6–C20 alkyl dimethyl ammonium chloride.

11. A method according to claim 10 wherein the quaternary biocide is a C8 to C22 benzyl dimethyl ammonium halide.

12. A method according to claim 1 wherein the biocidal efficacy of the quaternary biocide is protected by an "activity protector" selected from the group consisting of "enzyme stabilizers", "enzyme stabilizing systems", "micelle formation modifiers and inhibitors", and combinations thereof.

13. A method according to claim 12 wherein the biocidal efficacy of the quaternary biocide is protected by one or more enzyme stabilizers and stabilizer enhancers selected from the group consisting of boron compounds, polyols, formates, calcium ions, polyfunctional amino compounds, phosphates, citrates, sulphates and sequestering agents.

14. A method according to claim 13 wherein a stabilizer is selected from boric acid, boric oxide, borax, or sodium ortho-, meta-, or pyro-borate and perborates.

15. A method according to claim 14 wherein a stabilizer comprising sodium tetraborate.

16. A method according to claim 13 wherein the biocidal efficacy of the quaternary biocide is protected by a boron compound and further comprising a polyol having from 2 to 6 hydroxyl groups.

17. A method according to claim 16 wherein the polyol is selected from the group consisting of ethylene glycol, propylene glycol 1,2 propanediol, butyleneglycol, glycerol, mannitol, sorbitol, erythritol, glucose, fructose and lactose.

18. A method according to claim 17 wherein the polyol is selected from the group consisting of glycerol, mannitol, sorbitol, erythritol, glucose, fructose and lactose.

19. A method according to claim 12 wherein the biocidal efficacy of the quaternary biocide is protected by a micelle immiscible solvent.

20. A method according to claim 19 wherein the micelle immiscible solvent is selected from the group consisting of C1–C6 alkanols, C1–C6 diols, C3–C24 alkylene glycol ethers, alkylene glycol alky ethers, borates, lactates, citrates, tartrates and mixtures thereof.

21. A method according to claim 20 wherein the solvent comprises di (propylene glycol) methyl ether ("DPM").

22. A method according to claim 1 wherein the "activity protector" comprises boron ions.

23. A method according to claim 22 further comprising DPM.

24. A method according to claim 1 further comprising a non ionic surfactant.

25. A method according to claim 1 wherein the composition is being a shelf stable liquid disinfectant concentrate method containing at least 1% by weight of a quaternary biocide and capable of dilution with 20 parts of water to 1 part of concentrate, the diluted solution exhibiting a MIC after 24 hrs in the presence of up to 2% of tryptone (or the protein equivalent thereof) which is less than the MIC of a solution of the same concentration of the same quaternary biocide in distilled water in the presence of the same amount of the protein.

26. A method according to claim 25 wherein the protease is subtilisin.

27. A method according to claim 25 when diluted by more than 20 parts of water to 1 part of concentrate.

28. A method according to claim 27 when diluted by more than 100 parts of water to 1 part of concentrate.

29. A method according to claim 28 when diluted by more than 200 parts of water to 1 part of concentrate.

* * * * *

UNITED STATES PATENT AND TRADEMARK OFFICE
CERTIFICATE OF CORRECTION

| | |
|---|---|
| PATENT NO. | : 6,762,161 B2 |
| APPLICATION NO. | : 10/257088 |
| DATED | : July 13, 2004 |
| INVENTOR(S) | : Alex Sava et al. |

It is certified that error appears in the above-identified patent and that said Letters Patent is hereby corrected as shown below:

Col. 18 line 31, delete "comprising" and insert --comprises-- therefor.

Col. 18 line 59, delete "being".
Col. 18 line 60, delete "method".

Signed and Sealed this

Nineteenth Day of September, 2006

JON W. DUDAS
*Director of the United States Patent and Trademark Office*